(12) United States Patent
Sheridan et al.

(10) Patent No.: US 12,029,205 B2
(45) Date of Patent: *Jul. 9, 2024

(54) SYSTEMS AND METHODS FOR CONTINUOUS INSECT SENSING

(71) Applicant: Verily Life Sciences LLC, South San Francisco, CA (US)

(72) Inventors: Martin Sheridan, Redwood City, CA (US); Jianyi Liu, Santa Clara, CA (US); Matthew Metlitz, Menlo Park, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,863

(22) Filed: Jun. 27, 2023

(65) Prior Publication Data

US 2023/0329202 A1 Oct. 19, 2023

Related U.S. Application Data

(63) Continuation of application No. 16/520,017, filed on Jul. 23, 2019, now Pat. No. 11,716,976.

(Continued)

(51) Int. Cl.
*A01K 67/033* (2006.01)
*G06Q 50/02* (2012.01)
*A01K 29/00* (2006.01)

(52) U.S. Cl.
CPC ........... *A01K 67/033* (2013.01); *G06Q 50/02* (2013.01); *A01K 29/00* (2013.01)

(58) Field of Classification Search
CPC .............................. A01K 67/033; A01K 61/90
See application file for complete search history.

(56) References Cited

U.S. PATENT DOCUMENTS

| 4,898,108 A | 2/1990 | McDermott |
| 5,594,564 A | 1/1997 | Ishimoto et al. |

(Continued)

OTHER PUBLICATIONS

U.S. Appl. No. 16/520,017, "Non-Final Office Action", dated Sep. 7, 2022, 11 pages.

(Continued)

*Primary Examiner* — Monica L Perry
(74) *Attorney, Agent, or Firm* — Kilpatrick Townsend & Stockton LLP (57) ABSTRACT

Systems and methods for continuous insects sensing are described. One example method includes receiving a flow at a singulator, the flow comprising one or more insects; singulating the insects into a single-file flow of insects; sensing, using a sensor, insects within the single-file flow of insects; and incrementing a counter based on each sensed insects in the single-file flow of insects. One example system includes a channel defining a flow path for a flow of insects; a singulator positioned within the flow path and arranged to receive the flow of insects within the channel, the singulator configured to singulate the insects into a single-file flow of insects; a sensor positioned and arranged to sense insects in the single-file flow; and a processor in communication with the sensor and a non-transitory computer-readable medium, the processor configured to execute processor-executable instructions stored in the non-transitory computer-readable medium to receive sensor signals from the sensor; and count a number of insects based on the received sensor signals.

29 Claims, 8 Drawing Sheets

Related U.S. Application Data (60) Provisional application No. 62/703,085, filed on Jul. 25, 2018.

(56) References Cited

U.S. PATENT DOCUMENTS

| | | | |
|---|---|---|---|
| 5,594,654 | A | 1/1997 | Shuman et al. |
| 7,496,228 | B2 | 2/2009 | Landwehr et al. |
| 2003/0178285 | A1 | 9/2003 | Van Wijngaarden et al. |
| 2005/0011470 | A1 | 1/2005 | Skvorc, II |
| 2017/0071164 | A1 | 3/2017 | Zucker et al. |
| 2017/0360014 | A1* | 12/2017 | Hall ............... B65G 1/0492 |
| 2018/0206473 | A1 | 7/2018 | Massaro et al. |
| 2020/0029541 | A1 | 1/2020 | Sheridan et al. |
| 2020/0281176 | A1* | 9/2020 | Whitaker ............ A01K 67/033 |
| 2020/0359608 | A1 | 11/2020 | Du et al. |
| 2021/0008600 | A1 | 1/2021 | Greeley |
| 2022/0254182 | A1 | 8/2022 | Livne et al. |

OTHER PUBLICATIONS

U.S. Appl. No. 16/520,017, "Notice of Allowance", dated Mar. 16, 2023, 9 pages.

International Patent Application No. PCT/US2019/043239, "International Search Report and Written Opinion", dated Nov. 14, 2019, 17 pages.

International Patent Application No. PCT/US2019/043239, "Invitation to Pay Additional Fees and, Where Applicable, Protest Fee", dated Sep. 11, 2019, 2 pages.

Sarpola et al., "An Aquatic Insect imaging System to Automate Insect Classification", Transactions of the ASABE, vol. 51, 2008, pp. 2217-2225.

Singapore Patent Application No. SG11202100666Q, "Written Opinion", dated Aug. 10, 2022, 7 pages.

Singapore Application No. 11202100666Q, "Notice of Decision to Grant", dated Oct. 5, 2023, 6 pages.

* cited by examiner

SYSTEMS AND METHODS FOR CONTINUOUS INSECT SENSING

CROSS REFERENCE TO RELATED APPLICATION

This application is a continuation of U.S. patent application Ser. No. 16/520,017, filed Jul. 23, 2019, titled "Systems and Methods for Continuous Insect Pupae Sensing," which claims the benefit of U.S. Application No. 62/703,085, filed Jul. 25, 2018, titled "Systems And Methods For Continuous Insect Pupae Sensing," which are incorporated herein by reference in their entireties.

FIELD

The present disclosure relates generally to the mass-rearing of insects. More specifically, but not by way of limitation, this disclosure relates to systems and methods for continuous insect pupae sensing.

BACKGROUND

The mass-rearing of insect larvae can be very labor intensive. A lab technician may manually add a number of eggs or insect larvae to a plastic tray and determine the amount of food and water to add into the tray for the insect larvae. The lab technician may hand carry the plastic tray to a storage area to store the plastic tray. Periodically, the lab technician may perform observations on the insect larvae in the plastic tray or add food and water as needed. After the larvae mature into pupae, they may be moved from the larval rearing environment into another environment where they can mature into adult insects for release into the wild. Each of these steps may involve significant amounts of human labor, such as manually moving and emptying containers, sterilizing reusable components, etc.

SUMMARY

Various examples are described for systems and methods for continuous insect pupae sensing. For example, one example method includes receiving a flow at a singulator, the flow comprising one or more insect pupae; singulating the insect pupae into a single-file flow of insect pupae; sensing, using a sensor, insect pupae within the single-file flow of insect pupae; and incrementing a counter based on each sensed insect pupa in the single-file flow of insect pupae.

One example system includes a channel defining a flow path for a flow of insect pupae; a singulator positioned within the flow path and arranged to receive the flow of insect pupae within the channel, the singulator configured to singulate the insect pupae into a single-file flow of insect pupae; a sensor positioned and arranged to sense insect pupae in the single-file flow; and a processor in communication with the sensor and a non-transitory computer-readable medium, the processor configured to execute processor-executable instructions stored in the non-transitory computer-readable medium to receive sensor signals from the sensor; and count a number of insect pupae based on the received sensor signals.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of systems and methods for continuous insect pupae sensing. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

When mass rearing insects, it may be desirable to track the efficacy of the breeding program to ensure high yields or to identify problems quickly so they can be addressed. Examples according to this disclosure can provide accurate counting of insect pupae, such as during a transfer of pupae from one rearing environment to another.

In an illustrative example, insect pupae (or simply "pupae") from one rearing environment are flowed through a channel to a singulator. To do so, the pupae along with a fluid, such as water from their then-current rearing environment are dispensed into a channel, which flows through a singulator. The singulator is a mechanical device that reduces a large flow of pupae and fluid to a substantially single-file line of pupae within the fluid flow. The single-file line of pupae then passes a sensor, which sense each pupae and provides a sensor signal to a computing device. The computing device then counts each pupa. In addition, depending on the sensor employed, characteristics of the pupae may be sensed, such as size, sex, or any physical anomalies present in the pupae, such as deformities, growths, that a pupa is dead, etc.

In this example, the sensor is a camera that continuously films the single-file flow of pupae within a sensor area of the singulator. The images captured by the camera are provided to a recognition system executed by the computing device that can detect the presence of an insect pupa in an image. Using optical flow techniques, the recognition system can track movement of the pupa through the sensor area, detect the arrival of a new pupa, and the departure of the first pupa, thus enabling an accurate count of insect pupae. In addition, the recognition system detects the size, sex, and any physical anomalies on each pupa as it passes through the sensor area. The computing device then creates a record for each sensed pupa, including one or more captured images of the pupa as well as determined information about the pupa and its respective counted number within the cohort of insect pupa that passes through the singulator. The computing device may also store a batch or container number from which the pupa was obtained or a batch or container number into which the pupa is dispensed.

Such a configuration may allow not only an accurate counting of the pupae, but also per-pupa tracking from origination to destination. This may enable the system to track each reared insect from egg to maturation into an adult insect and, if the insect is male, release, or, if the insect is female, disposal. Thus, if anomalies are present in a threshold number of pupae from particular container, the rearing program can detect a potential problem and potentially trace it back to a point earlier in the rearing process and address any issues that may be present. In addition, such systems and methods for continuous insect pupae sensing according to this disclosure may enable a fully automated counting and transfer process from one rearing environment to another. Transfer of insect populations between different containers can be a highly labor intensive process, involving dozens of persons to properly handle and process each population, including associated record keeping.

This illustrative example is given to introduce the reader to the general subject matter discussed herein and the disclosure is not limited to this example. The following sections describe various additional non-limiting examples and examples of systems and methods for continuous insect pupae sensing.

Figure 1:
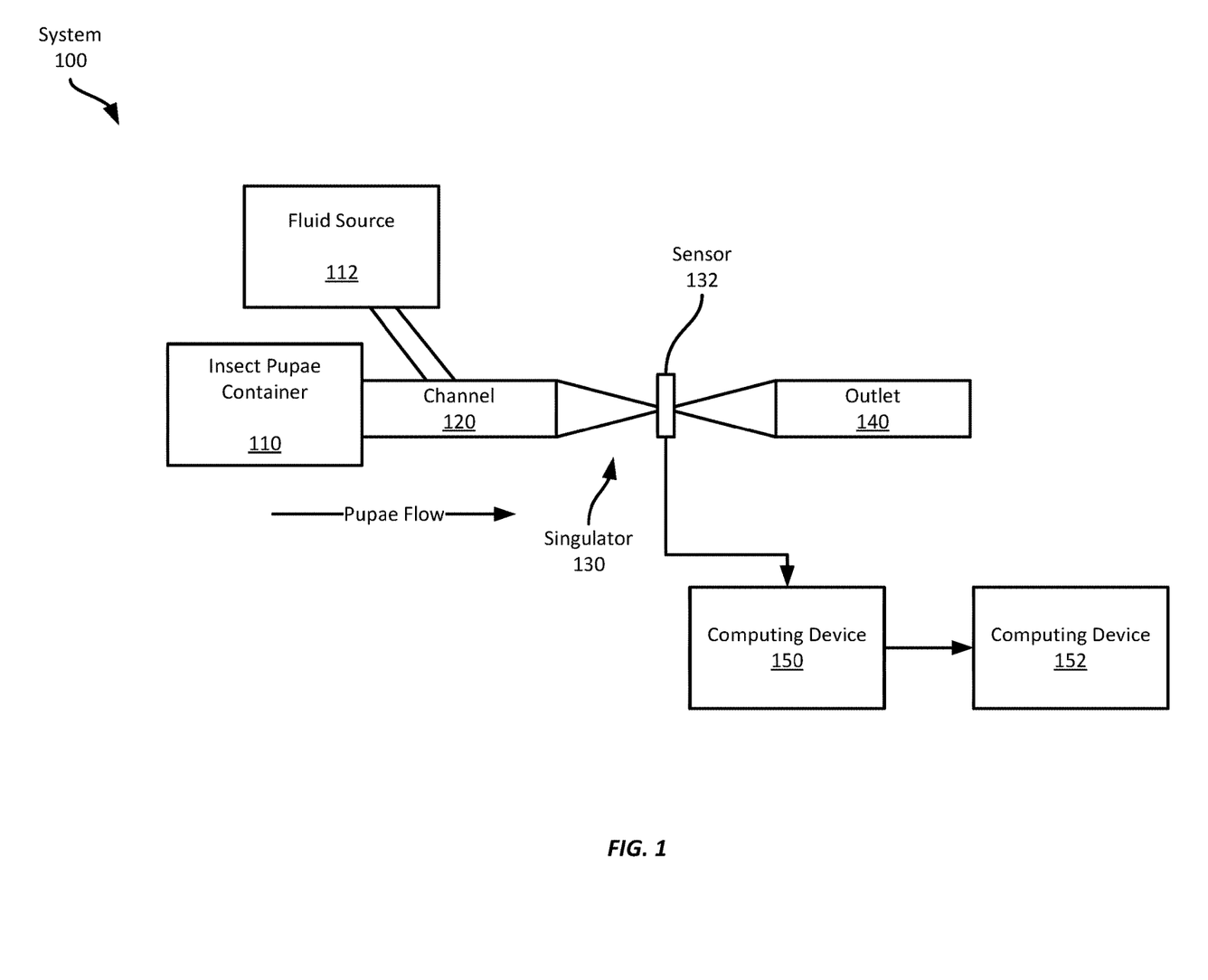
FIGS. 1-3 show example systems for continuous insect pupae sensing according to this disclosure.

Referring now to FIG. 1, FIG. 1 shows an example system 100 for continuous insect pupae sensing. The system 100 includes an insect pupae container 110 in which a population of insect pupae is maintained. The container 110 is physically connected to one end of a channel 120 that can receive a flow of pupae from the insect pupae container 110 and, in this example, fluid from the fluid source 112 (discussed in more detail below). The other end of the channel 120 is connected to one end of a singulator 130, which narrows the width of the channel to enable singulation of insect pupae for sensing. Examples of suitable singulators 130 will be discussed in more detail below with respect to FIGS. 4A-4B and 5-6.

A sensor 132 is positioned and arranged to sense insect pupae in the single-file flow created by the singulator 130, and the other end of the singulator 130 is connected to an outlet 140 where the singulated insect pupae may be transferred to another container. In this example, the singulator 130 widens to the width of the outlet, though such a configuration is not required. The sensor 132 is in communication with a computing device 150, which is in communication with a second computing device 152. The computing devices 150, 152 collectively execute software to receive sensor signals from the sensor 132, count the insect pupae passing through the singulator 130, and, in some examples, determine one or more characteristics of one or more of the insect pupae based on the sensor signals.

The example system 100 shown in FIG. 1 employs two computing device 150, 152, though it should be appreciated that a single computing device may be employed in some examples, or more than two computing devices may be used to further apportion various processing tasks. In this example, computing device 150 receives sensor signals, determines when an insect pupae is present in the singulator based on the received sensor signals, increments a count associated with the insect, and determines one or more characteristics of the pupae, such as its size or its sex. It may then transmit the count and the characteristic information to the second computing device 152, which may aggregate such information. In some examples, however, the computing device 150 may provide more particularized functionality.

For example, computing device 150 may receive sensor signals from the sensor 132 and may simply store the received sensor signals or information extracted from the received sensor signals. Later the computing device 150 may provide the extracted information or the stored sensor signals to the second computing device 152, which may then analyze it to determine a number of insect pupae detected and, in some examples, one or more characteristics of the detected insect pupae. Such an example may be employed where the computing device has limited processing capabilities, but is provided with substantial memory. However, in some examples, computing device 150 may be a specialized computing device, such as an FGPA or DSP, that is configured to process received sensor data, e.g., image data, to detect insect pupae and to processing sensor information, e.g., images, to determine one or more characteristics of the detected insect pupae. For example, the specialized computing device may be an FPGA with a machine learning technique, e.g., a neural network, that has been trained to recognize one or more characteristics of insect pupae based on an input image. The output of the machine learning technique may then be provided to the second computing device 152 which may store the characteristics as well as maintain a count of the total number of insect pupae (or the number of insect pupae having one or more particular characteristics). Thus, some examples may split processing amongst multiple computing device, including the use of specialized computing devices, to distribute processing requirements.

In this example, the sensor 132 includes one or more light emitters and one or more photodetectors, e.g., a photodiode, photoresistor, phototransistor, etc., arranged on opposite sides of the singulator from each other. The light emitter(s) emits light across the singulator towards the photodetector(s), which detects the amount of incoming light received and transmits signals to the computing device 150 indicating the amount of incoming light detected. When an insect pupae passes through the singulator, it obstructs some of the emitted light, reducing the amount of light received by the photodetector. The computing device 150 may interpret such a reduction in light as an insect pupae. For example, if the amount of detected light is reduced below a preset threshold, the computing device 150 may interpret the sensor signal(s) as indicating the presence of an insect pupae.

While a light emitter/photodetector sensor is described above, other suitable sensors 132 may be employed, such as image sensors (e.g., a camera), a capacitive sensor, or an ultrasound emitter and detector. For example, a camera may be oriented to capture images of the interior portion of the singulator 130 and capture images of insect pupae as they pass through the singulator 130. Captured images may be transmitted to the computing device 150, which may provide the images to an image recognition technique to recognize when an insect pupae is present in the singulator. Such a technique may also include an optical flow technique that may determine the movement of the insect pupae through the singulator, which may prevent the processor from double (triple, etc.) counting the pupae. Other less computationally expensive techniques may be used instead. For example, the camera may detect an average brightness or an average color within the image over one or more control images, or via a preset threshold, and when a captured image has an average brightness that dips below the threshold, or changes color by a threshold amount, the computing device(s) 150, 152 may determine that an insect pupae has passed through the singulator 130.

In some examples, a capacitive sensor may be employed. Such a sensor may change output a signal to the computing device 150 indicating the capacitance measured by the sensor. When an insect pupae passes over the sensor, it may cause the capacitance to change. When the computing device 150 detects that the capacitance has changed by a threshold amount, it may determine that an insect pupae is present in the singulator 130. Alternatively, an ultrasound emitter and detector may be arranged to emit ultrasound into the singulator and capture reflected ultrasound waves. The ultrasound detector may transmit one or more sensor signals to the computing device 150, which may determine a magnitude or frequency of the reflected ultrasound waves. If the magnitude or frequency changes by a threshold amount, the computing device 150 may determine that an insect pupae is present in the singulator 130.

In some examples, rather than detecting reflected ultrasound waves, the ultrasound emitter and detector may be positioned on opposing sides of the singulator 130 such that the ultrasound emitter emits ultrasound waves across the singulator towards the ultrasound detector. The ultrasound detector may then transmit sensor signals to the computing device 150 based on the detected ultrasound waves. When an insect pupae passes through the singulator, it may obstruct the emitted ultrasound waves, causing a change in the detected ultrasound waves at the ultrasound detector. The computing device 150 may then determine the presence of an insect larvae based on sensor signals from the ultrasound detector indicating a change in the characteristics of received ultrasound waves (e.g., a frequency, magnitude, etc.).

In this example, the system 100 also includes a fluid source 112 that can be used to supply additional fluid to the channel 120. The fluid source can be employed to provide a substantially constant fluid pressure within the channel 120 and onto the singulator 130, which may help ensure the singulator 130 operates correctly and to prevent clogging or bunching of insect pupae. A fluid source 112 may be any source of fluid that can provide a substantially constant fluid pressure, such as a fluid pump in combination with a fluid reservoir, a refillable elevated container, a connection to a public water supply, etc. The fluid source may provide any suitable fluid, such as water.

While this example system 100 employs a fluid channel to transport pupae from the insect pupae container 110 to the singulator 130, other suitable transport mechanisms, such as conveyors may be employed as well. For example, channel 120 may be a conveyor having one or more conveyor belts onto which pupae from the insect pupae container 110 are dispensed. The singulator 130 may be positioned within the path of the conveyor such that the transported pupae are forced into and through the singulator 130, and past the sensor 132, by the conveyor. Such a conveyor may operate at a substantially constant speed to help ensure that the singulator does not clog or the insect pupae do not bunch together when entering the singulator. In some such examples, fluid from a fluid source 112 may be dispensed onto the conveyor to help separate insect pupae from each other, which may enable more accurate counting and characterizing of the pupae population. Alternatively, or in addition, insect pupae may be transferred from a conveyor into a fluid channel prior to reaching the singulator 130.

Figure 2:
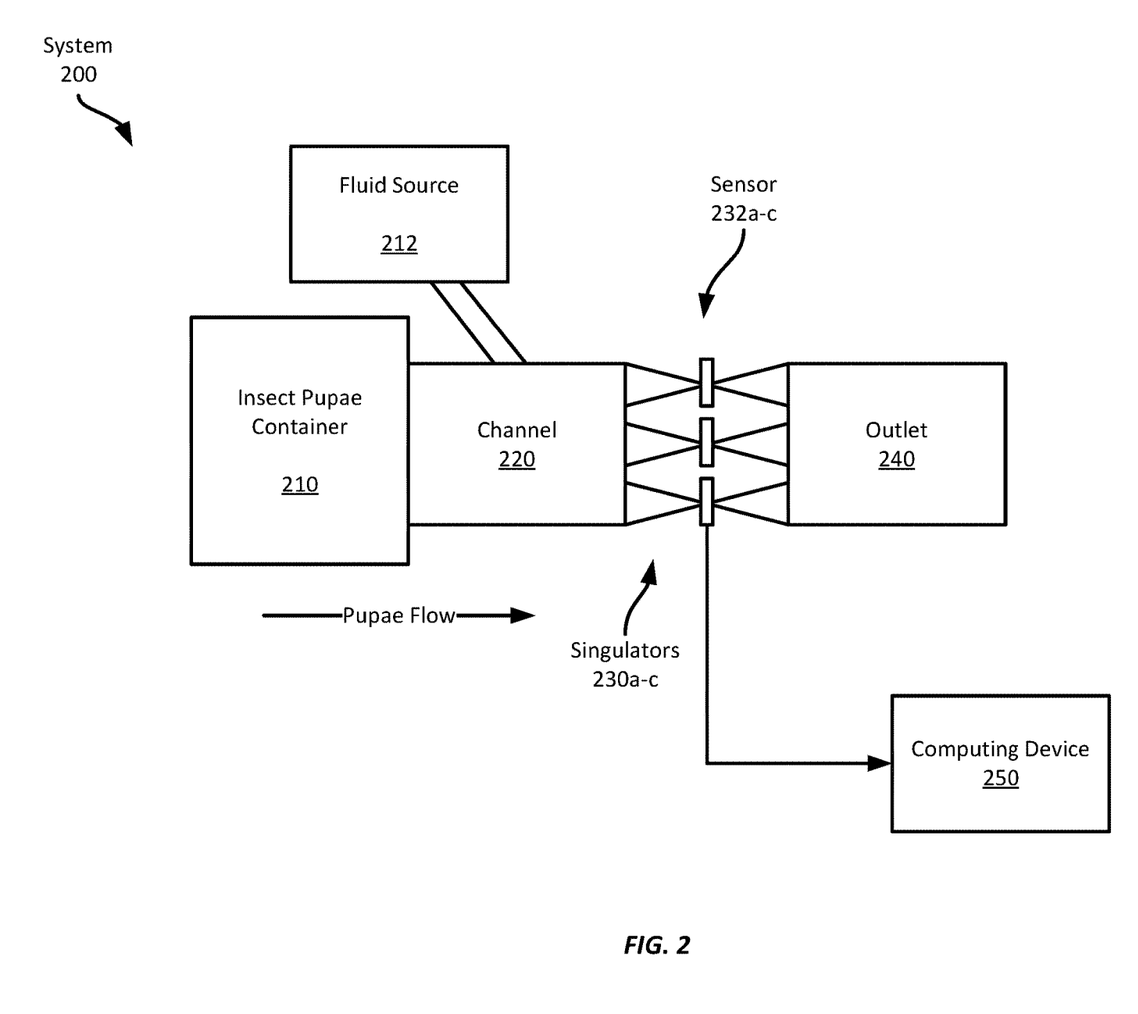

Referring now to FIG. 2, FIG. 2 shows another example system 200 for continuous insect pupae sensing. In this example, the insect pupae container 210 is connected to a channel 220 to transport insect pupae 220 to multiple singulators 230*a-c* that are arranged in parallel to each other, each of which has an associated sensor 232*a-c* to sense insect pupae passing through the respective singulator 230*a-c*. Example systems employing multiple singulators may enable a higher-volume of insect pupae to be counted and characterized within a given time period. And while the singulators 230*a-c* are depicted with a common outlet 240, each singulator 230*a-c* may output to a discrete outlet, or a number of shared outlets, such as to enable dividing the original insect pupae population into smaller subdivided populations. Further, while a single computing device 250 is depicted in this example, which receives sensor signals from each sensor 232*a-c*, in some examples, multiple computing devices 250 may be employed.

FIG. 2 describes the use of multiple singulators 230*a-c* in parallel with each other. It should be understood that "in parallel" is not used in the geometric sense. Rather, "in parallel" means the singulators are not arranged serially. Thus, each singulator 230*a-c* receives insect pupae from a channel rather than from another singulator 230*a-c*.

Figure 3:
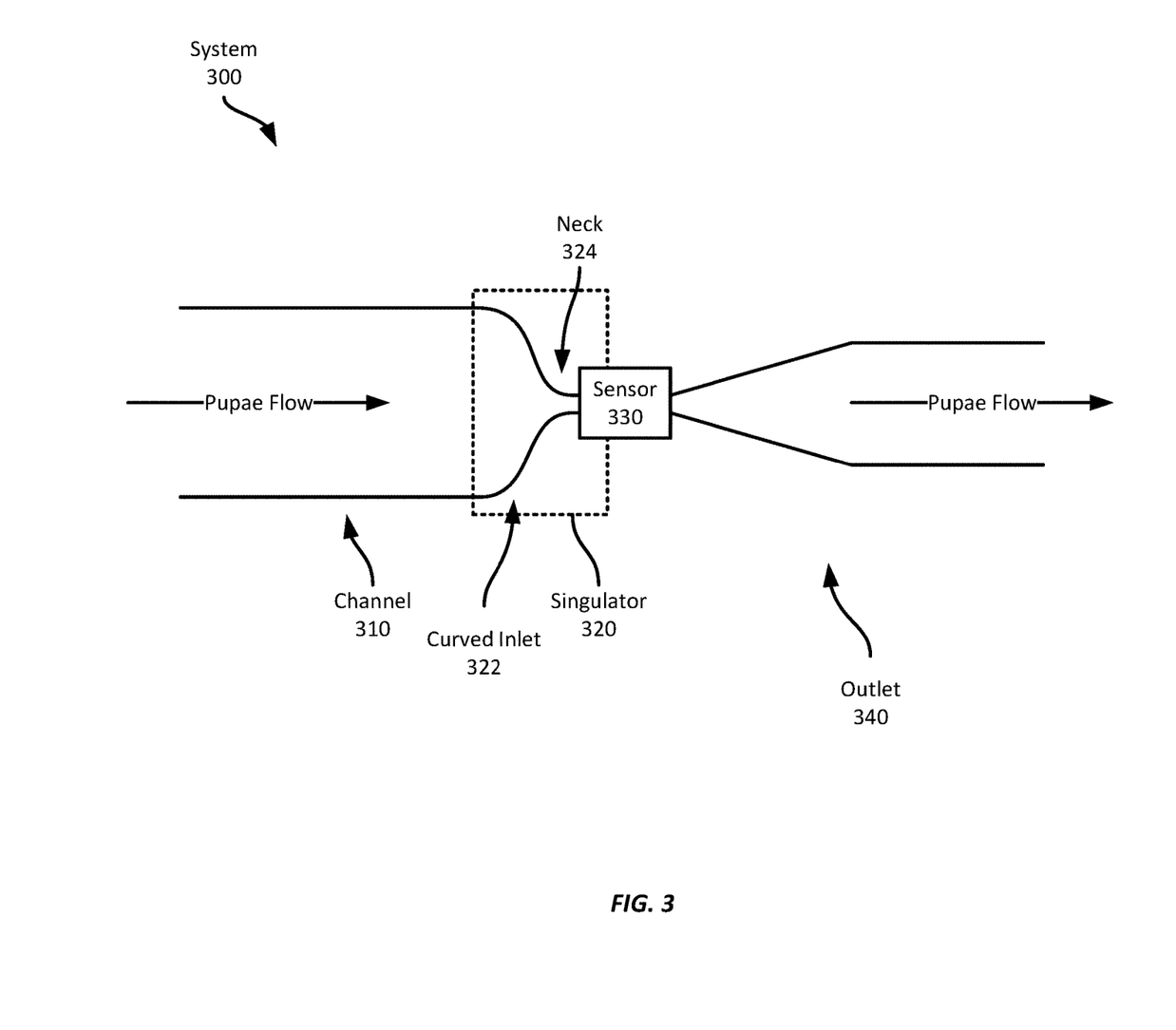

Referring now to FIG. 3, FIG. 3 shows an example singulator 300 for continuous insect pupae sensing. In this example, the singulator 300 has a generally hourglass shape with an inlet 322 connected to the channel 310 that provides a curved portion to narrow the width of the channel to a neck 324 sized to allow a single insect pupae to pass through the neck at a time. It should be noted that the curved inlet 322 lacks sharp corners or edges that may snag insect pupae, which may damage the pupae or cause multiple pupae to bunch together; however, in some examples, the inlet may have corners or uncurved edges.

The neck 324 provides a channel through which a single-file flow of pupae passes a sensor 330 before being transported to an outlet 340. In examples using a fluid flow, the neck portion 324 may be a fluid channel that is formed as a unitary piece with the curved inlet 322, channel 310, and outlet 340; however, in some examples, one or more of the channel 310, curved inlet 322, neck portion 324, and outlet 340 may be formed as discrete pieces and joined together using a suitable connecting means, such as an adhesive, welding, staples, screws, rivets, bolts, etc.

In some examples, singulators according to the example singulator 320 shown in FIG. 3 may perform more efficiently when the flow of insect pupae is provided with a substantially constant fluid pressure, such as described above with respect to FIG. 1. Such substantially constant fluid pressure may move pupae into and through the singulator, or may help prevent snagging or bunching of the pupae within the channel 310, curved inlet 322 or neck 324 portions of the singulator 320.

In examples employing a conveyor rather than a fluid channel, the singulator 320 may be positioned against the conveyor to enable insect pupae to interact with the singulator 320. Further, in some examples, a fluid may be introduced into the singulator 320 such as within the curved inlet to help separate or singulate insect pupae from each other or to prevent clogging or bunching of the insect pupae; however, use of a fluid is not required.

It should be appreciated that while only one singulator 300 is shown in this example, multiple such singulators may be arranged in parallel to receive the flow of insect pupae from the channel 310. For example, the singulator 300 shown in FIG. 3 may be incorporated into the system 200 shown in FIG. 2 in some examples.

Figure 4A:
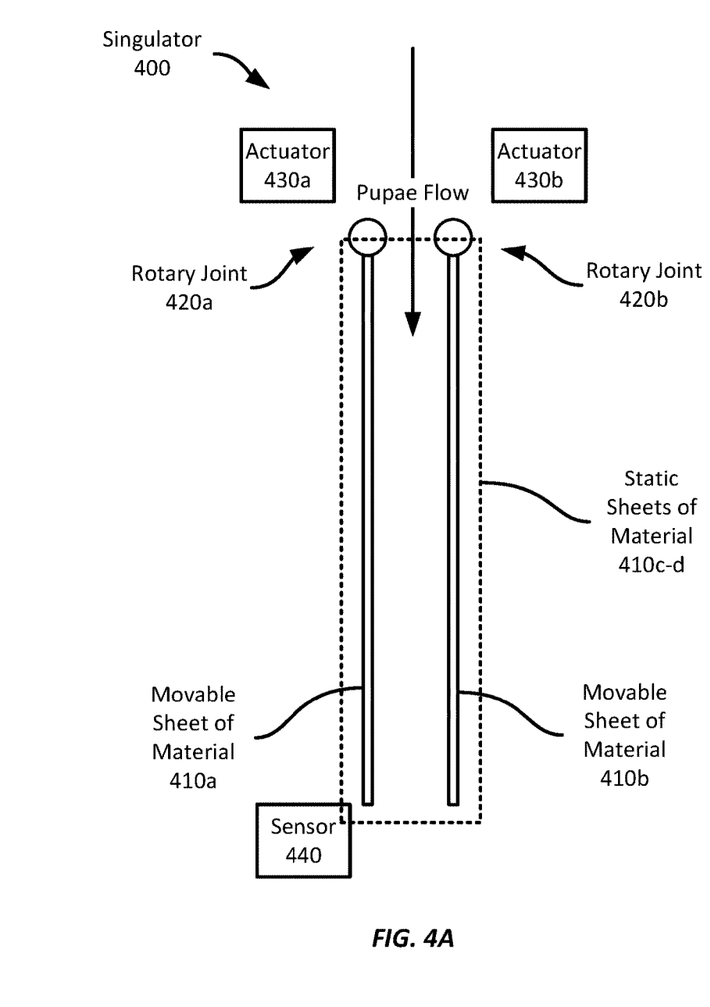
FIGS. 4A-4B and 5-6 show example singulators for continuous insect pupae sensing according to this disclosure.
Figure 4B:
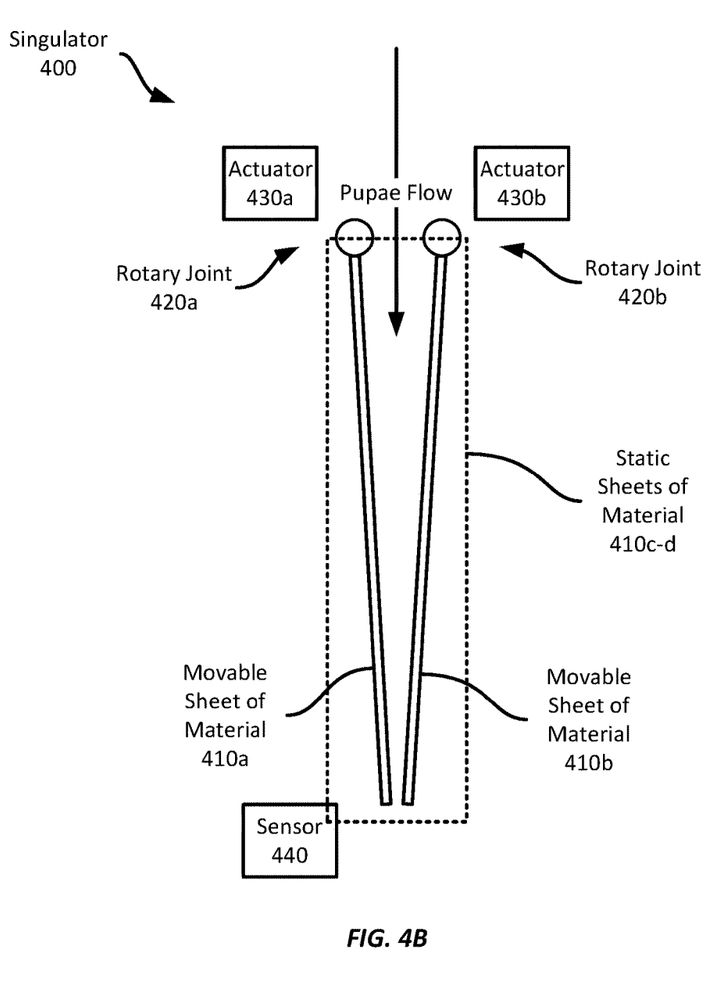

Referring now to FIGS. 4A-4B, FIGS. 4A-4B shows an example singulator 400 according to one example. In this example, the singulator 400 includes two movable sheets of material 410a-b that are positioned opposite each other to form a fluid channel between them, and a second pair of static sheets of material 410c-d, oriented perpendicular to, and in contact with, the movable sheets of material 410a-b. Each movable sheet of material is connected at one end to a respective rotary joint 420a-b, which are in turn coupled to a respective actuator 430a-b that can rotate the rotary joint and, consequently, its respective movable sheet of material 410a-b. In this example, the singulator is oriented so that the pupae flow is vertical and downward; however any suitable orientation may be employed.

FIG. 4A shows a cross-sectional view of one example configuration. In this example, the movable sheets of materials 410a-b are positioned in parallel planes and spaced apart by a few centimeters ("cm"), such as 2-3 cm. Each movable sheet of material 410a-b in this example is approximately 5 cm tall (in the direction of pupae flow), and approximately 10 cm wide (in a direction perpendicular to the plane of the drawing). In this example, the sheets of material are constructed of a transparent or translucent plastic material that may provide backlighting to an imaging system that may enhance the quality of captured images; however, any suitable material may be employed, including glass, acrylic, polyvinyl chloride ("PVC"), etc. In some examples, the movable sheets of material 410a-b are non-porous and non-absorbent, though porous or absorbent materials may be employed in some examples.

In addition to the movable sheets of material 410a-b, the singulator also includes two additional static sheets of material 410c-d (shown with dashed lines) positioned in planes perpendicular to the movable sheets of material 410a-b. The static sheets of material 410c-d form additional boundaries for the fluid channel defined between the movable sheets of material 410a-b. Thus, in this example, the movable sheets of materials 410a-b are in contact with the static sheets of material 410c-d, but are not affixed to them. Rather the movable sheets of material 410a-b are configured to rotate about their respective rotary joints 420a-b, as will be discussed in more detail below. The contact between the movable and static sheets of material 410a-d may or may not be fluid tight; however, the contact is sufficient to prevent movement of an pupa through any gap between a moveable sheet of material 410a-b and a static sheet of material 410c-d, thereby preventing escape of a pupa through such a gap. The static sheets of material 410c-d may be formed of any suitable material, such as any of those discussed above with respect to the movable sheets of material 410a-b.

As discussed above, the movable sheets of material 410a-b are coupled to a respective rotary joint 420a-b, such as a hinge. The actuators 430a-b are configured to rotate the movable sheets of material 410a-b around their respective rotary joint 420a-b between to positions. And while two actuators are shown in this example, one actuator may be sufficient in some examples, or more than two actuators may be employed, as needed. The first position is shown in FIG. 4A, in which the two movable sheets of material 410a-b are substantially parallel to each other, thereby forming a gap between them having a substantially constant width. In the second position, the two movable sheets of materials 410a-b are oriented such that the distal ends of the movable sheets of material 410a-b are nearer each other than the proximal ends, which are affixed to the rotary joints 420a-b, thereby forming a wedge-shaped gap. In this example, the second position, illustrated in FIG. 4B, provides a distal opening approximately the width of an average pupa of an insect pupae population. For example, if the insect pupae population includes *Aedes aegypti* pupa, the distal gap shown in FIG. 4B is approximately the width of an average *Aedes aegypti* pupa. However, any suitable gap may be employed according to design requirements.

In this example, a sensor 440 is positioned adjacent to the distal gap formed by the movable sheets of material 410a-b to sense pupae as they pass through the distal gap. In this example, the sensor 440 is a camera that captures video images of the distal gap as pupae fall through the gap. The captured images are transmitted to a computing device (not shown), which employs an image recognition technique to recognize and count individual insect pupae, as well as an optical flow technique to ensure insect pupae are counted only once. In addition, the computing device may also detect one or more characteristics of one or more of the insect pupae, such as the characteristics discussed above (e.g., size, shape, sex, etc.).

In this example, the actuators 430a-b are stepper motors coupled to a respective rotary joint 420a-b. The actuators 430 are controlled by the computing device and move between the two positions shown in FIGS. 4A-4B in response to signals transmitted by the computing device. In this example, the computer outputs a signal to cause the actuators 430a-b to move the movable sheets of materials 410a-b into the first position shown in FIG. 4A between populations of insect pupae. For example, the first position may be employed to flush the singulator 400 with a fluid, such as water, to prepare the singulator for the next pupae population. The computing device then outputs another signal to cause the actuators 430a-b to move the movable sheets of materials 410a-b into the second position shown in FIG. 4B to receive a population of insect pupae.

When configured as shown in FIG. 4B, the singulator receives a flow of insect pupae, such as in a fluid medium like water. The flow of insect pupae enters the top of the singulator, between the rotary joints 420a-b and descends through the fluid channel defined by the sheets of material 410a-d to the narrow gap at the bottom. The insect pupae then pass through the distal gap and pass by the sensor 440, which detects each insect pupa and transmit sensor signals to the computing device, which counts each insect pupa and, in some examples, determines one or more characteristics of detected insect pupae. As the pupae flow through the singulator, additional fluid may flow into the singulator to help the insect pupae move downward through the singulator 400, though such additional fluid flow is not required in some examples. It should be appreciated that, while the distal gap has a width based on an average pupa size for a predetermined insect pupae population, multiple insect pupae may pass through the distal gap at a time, separated along the length of the distal gap. To enable sensing of the insect pupae passing through the distal gap, the sensor 440 may include multiple sensor elements, such as multiple light emitters or detectors, or a camera may be positioned to capture the entire length of the distal gap.

After the entire population of insect pupae has passed through the singulator, the singulator may again return to the first position shown in FIG. 4A, where it may be flushed again with a fluid in preparation for the next population of insect pupae.

Figure 5:
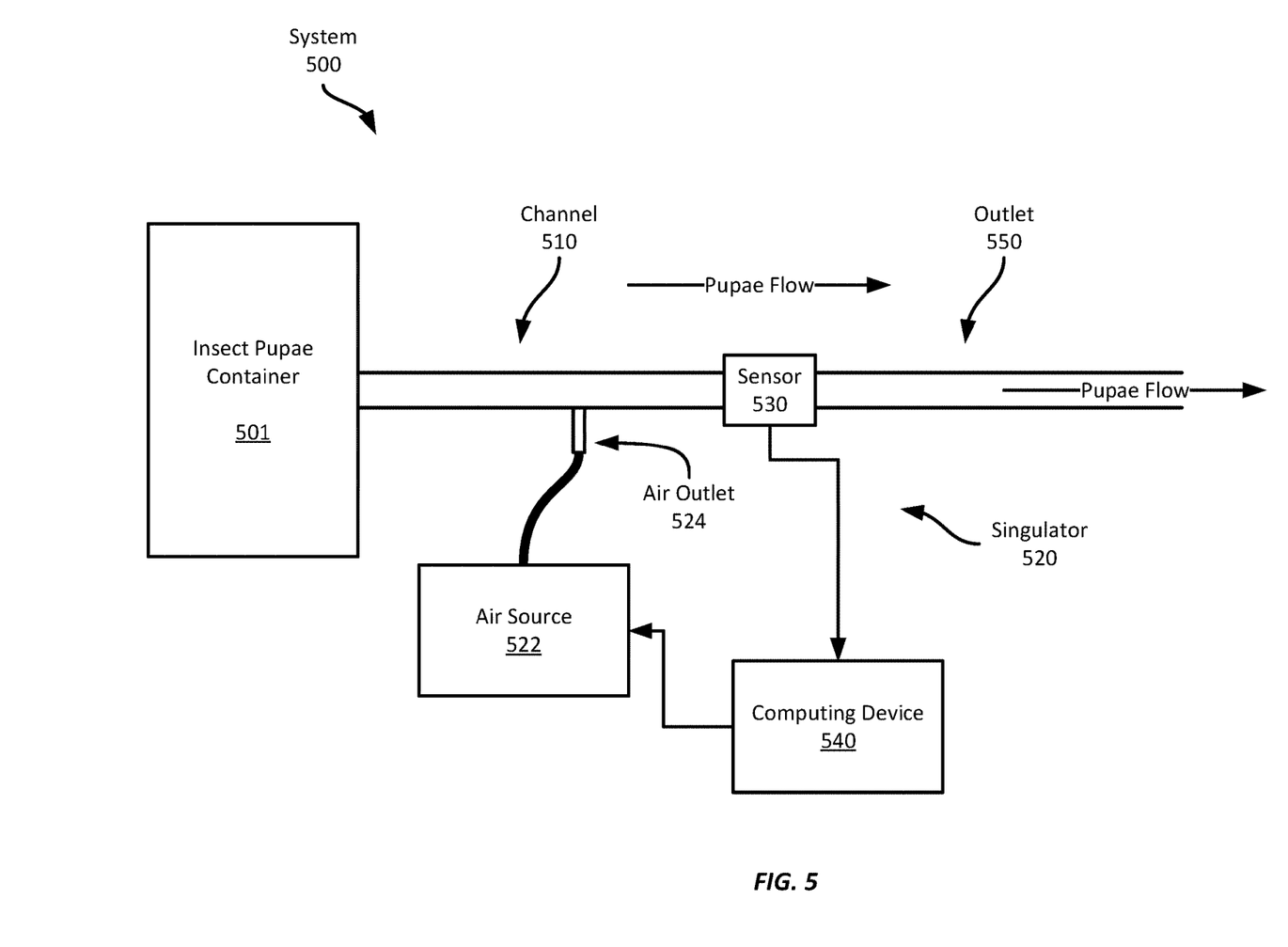

Referring now to FIG. 5, FIG. 5 shows an example system 500 for continuous insect pupae sensing. In this example, the system 500 includes an insect pupae container 501 connected to a channel 510. In a side edge of the channel 510, an air outlet 524 is positioned to blow pressurized air into the channel, thereby creating one or more air bubbles within a fluid flowing through the channel 510. The air outlet 524 is connected by an air hose to a pressurized air source 522, such as an air tank or air pump. A sensor 530 is positioned above or within the channel 510 and is oriented to sense insect pupae flowing through the channel 510 and past the sensor 530, and to send sensor signals to the computing device 540. The channel 510 proceeds past the sensor 530 and into an outlet 550.

In this example, the singulator 520 includes the air source 522 and the air outlet 524. The singulator 520 singulates insect pupa within the channel 510 by creating a series of air bubbles in a fluid flowing through the channel. The air bubbles may be interspersed between insect pupae, thereby separating and singulating them. Specifically, the surface tension in the fluid created by the air bubble may prevent the insect pupae from passing around the bubble or otherwise escaping from the fluid region between successive bubbles, thereby ensuring that the insect pupae arrives at the sensor alone, rather than having moved into an adjacent pupae's fluid region. It should be appreciated, however, that the singulator 520 shown in FIG. 5 may be incorporated into other singulators according to this disclosure, such as the examples shown in FIGS. 1-4. To create such a combination, the air outlet 524 may be positioned within, for example, the curved inlet 322 or neck portion 324 of the singulator 300 shown in FIG. 3 to further help separate and singulate insect pupae flowing through the singulator. Similarly, with respect to FIG. 4, one or more air outlets 524 may be positioned near a distal end of one or both movable sheets of material 410a-b to create air bubbles in a fluid flow of insect pupae passing through the singulator 400. The introduction of air bubbles in such an example may further help separate and singulate insect pupae, and may assist movement of the pupae through the distal gap.

In this example, the air outlet or pressurized air source are computer controlled to create air bubbles only in response to a signal output by a computing device. For example, the computing device may control an actuator to open and control a valve to control the flow of pressurized air from the air outlet 524. However, in some examples, the pressurized air source 522 may simply provide a substantially constant air pressure at the air outlet to create a substantially constant stream of air bubbles in a fluid flow.

In this example, the sensor 530 is a camera oriented to capture images or video of the flow of insect pupae past the sensor 530. The captured images may then be transmitted to a computing device 540 to detect individual insect pupae, count them, and in some examples, determine one or more characteristics of the insect pupae. And while this example employs a camera, the sensor 530 may be any suitable sensor, such as any discussed above.

Figure 6:
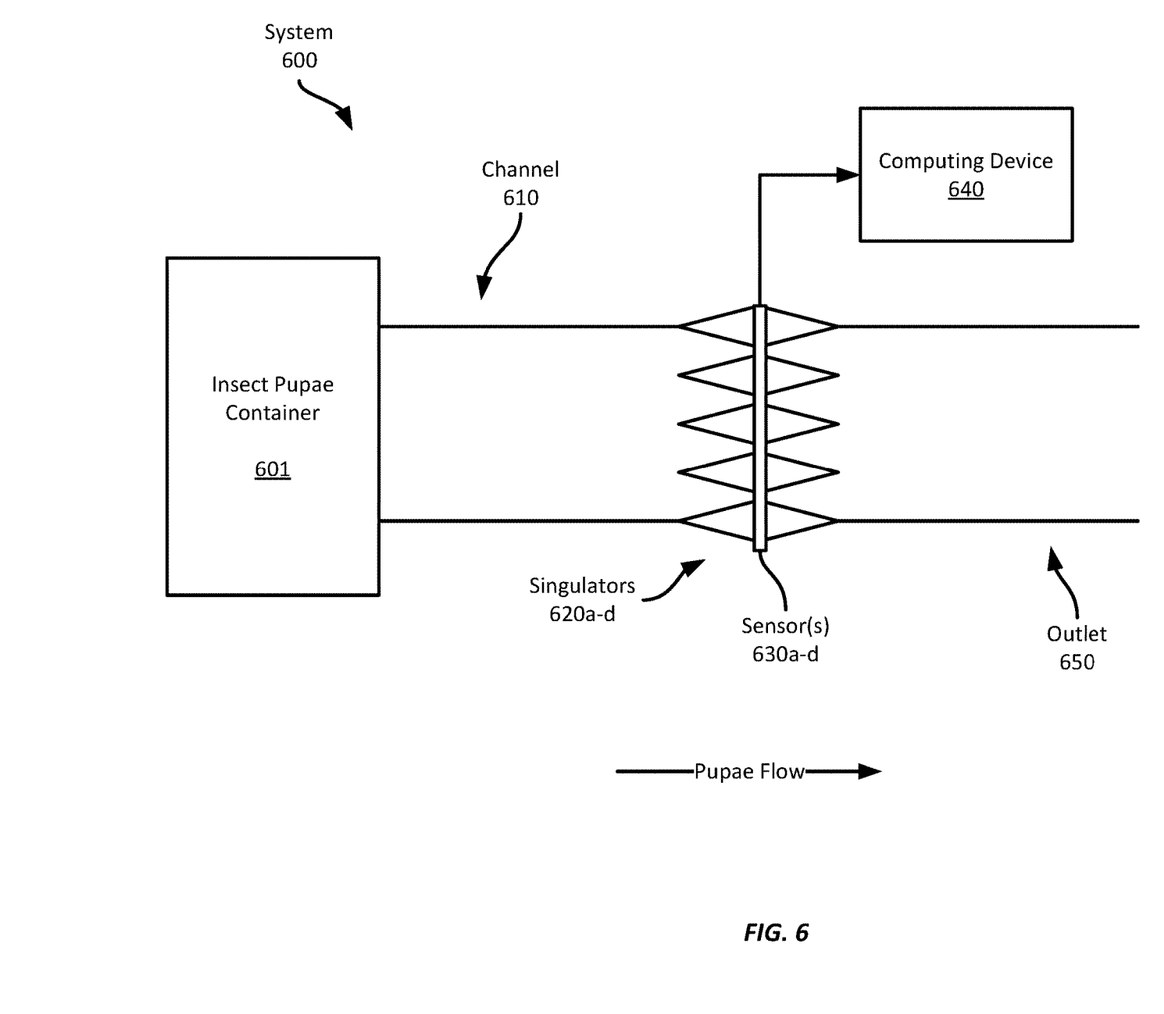

Referring now to FIG. 6, FIG. 6 shows an example system 600 for continuous insect pupae sensing. The system 600 includes an insect pupae container 601 connected to a channel 610. A singulator structure having multiple singulators 620a-d is positioned to receive a flow of insect pupae from the channel 610 and to singulate the insect pupae flowing through the channel. The singulators 620a-d are arranged in parallel and form a manifold structure, similar to the system 200 shown in FIG. 2. This singulators 620a-d may be any suitable singulator according to this disclosure; however, in this example, the singulators 620a-d are formed as wedges to narrow the flow of insect pupae to allow only a single pupae past the respective sensor 630a-d of a particular singulator 620a-d. The singulators 620a-d then output the insect pupae into an outlet 650, where they may be collected or moved to another rearing environment.

The sensors 630a-d provide sensor signals to the computing device 640, which counts insect pupae based on the received sensor signals and, in some examples, may determine one or more characteristics of pupae within the flow of insect pupae. In this example, the sensors 630a-d each include a camera, which captures images or video of insect pupae passing through a respective singulator 620a-d; however, any suitable sensor according to this disclosure may be employed.

Figure 7:
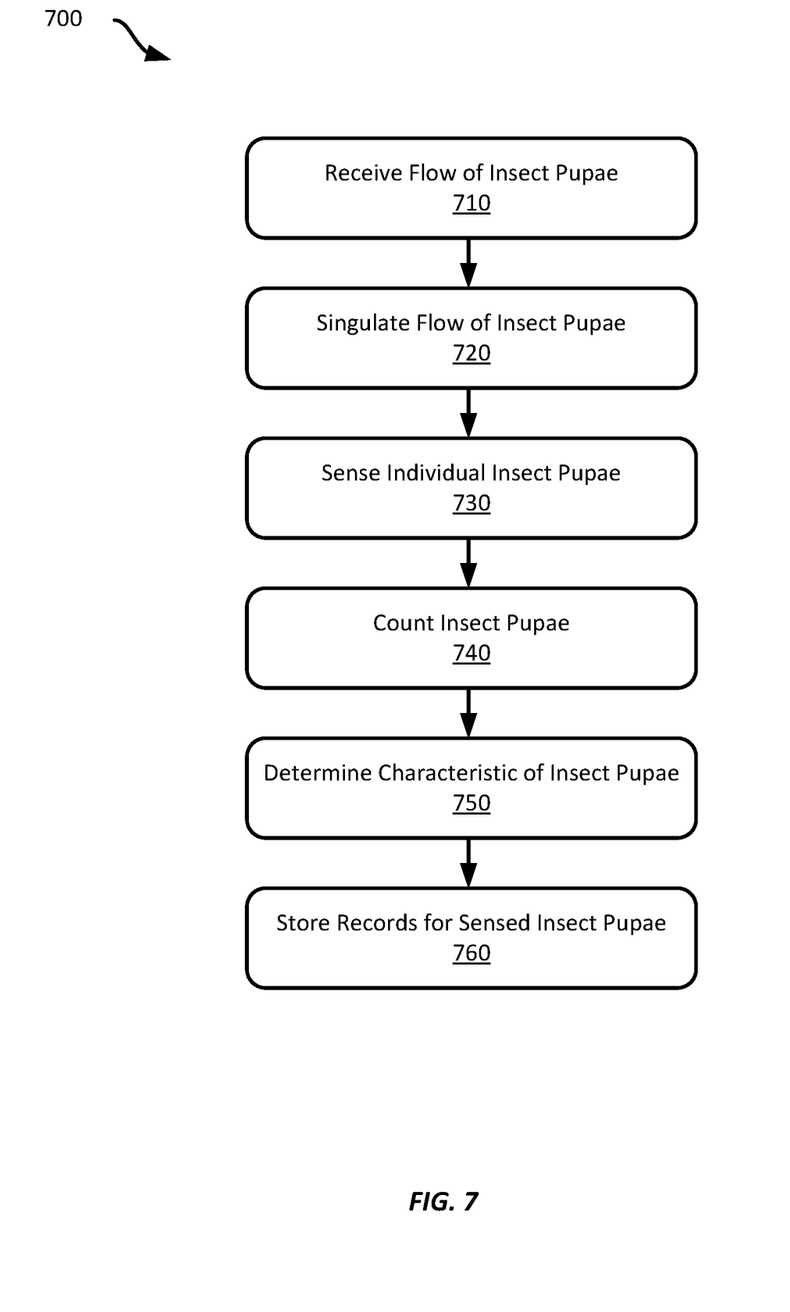
FIG. 7 shows a flowchart for an example method for continuous insect pupae sensing according to this disclosure.

Referring now to FIG. 7, FIG. 7 shows an example method 700 for continuous insect pupae sensing according to this disclosure. The example method 700 will be discussed with respect to the system 100 shown in FIG. 1; however, it should be appreciated that any suitable system for continuous insect pupae sensing may be employed.

At block 710, the channel 120 receives a flow of insect pupae from the insect pupae container 110. In addition, fluid is dispensed from the fluid source 112 into the channel 120 to help move the insect pupae through the channel to the singulator 130. The flow of insect pupae, including the fluid, is then received by at the singulator 130. While a fluid flow of insect pupae is employed in this example, it should be appreciated that the flow may be transported to the singulator by a conveyor device, as discussed above.

At block 720, the singulator singulates the insect pupae into a substantially single-file flow of insect pupae. As discussed above, any suitable singulator according to this disclosure may be employed, such as any of the singulators disclosed above with respect to FIGS. 3-6. In one example employing the singulator 400 shown in FIGS. 4A-4B, prior to block 720, the movable sheets of material 410a-b may be moved into the second position shown in FIG. 4B to create a distal gap sized to the width of an average insect pupa of the insect pupae population, as discussed above.

At block 730, the system 100 senses, using the sensor 132, insect pupae within the single-file flow of insect pupae. In one example, a light sensor may detect variations in light intensity as insect pupae pass the sensor. In an example employing a camera, the camera may capture images or video of insect pupae flowing through the singulator 130 and transmit the captured images or video to the computing device 150, which may then employ an image recognition technique to sense individual insect pupae. In one such example, the computing device may further employ an optical flow technique to prevent duplicate sensing of a single insect pupa.

At block 740, the computing device 150 increments a counter based on each sensed insect pupae in the single-file flow of insect pupae. In this example, the computing device 150 resets its counter before a new flow of insect pupae is flowed into the channel 120 and through the singulator 130; however, in some examples, the computing device 150 may maintain a running count of all sensed insect pupae from multiple populations of insect pupae.

At block 750, the computing device 150 determine one or more characteristics of one or more insect pupae. In this example, the computing device 150 determines the one or more characteristics based on one or more received sensor signals. For example, if the sensor is a camera, the computing device 150 may employ one or more image recognition techniques, which may include one or more trained machine-learning models, to recognize characteristics of an insect pupa. For example, the computing device 150 may determine a size of an insect pupae based on a width of the insect pupae in pixels within the image, or based on a distance between a head and tail of the insect pupae using the image recognition technique. The computing device may determine a sex of an insect pupa based on one or more physical characteristics. For example, *Aedes aegypti* pupae exhibit sexual dimorphism, enabling an image recognition technique to identify physical characteristics indicative of either a male or female insect pupa, which include size or other physical features of the insect pupae. In some examples, the computing device 150 may be able to identify anomalies in an insect pupa, such as an abnormal growth or whether the pupa is intact, damaged, alive, or dead. For example, one or more missing body parts may indicate physical damage to the pupa or may indicate that the pupa is likely dead. An image recognition technique may detect an abnormal growth based on difference between a normal pupa shape or outline and the shape or outline of a pupa in a captured image.

In some examples, characteristics may be determined using other types of sensors. For example, one or more light detectors may be employed to determine a size of an insect pupa, such as based on a number of light detectors detecting a reduction in received light, or an amount of change in received light. If the sensor 132 employs a 10×10 grid of light sensors, an insect pupa that obstructs a 5×3 portion of the grid may indicate one size, while an insect pupa that obstructs a 6×4 portion o the grid may indicate another size. Further, the computing device 150 may determine a characteristic, such as a sex of an insect pupa based on such information. For example, in examples where female pupae of an insect species are larger than the male pupae, differences in sized may be employed to determine a sex of a particular pupa (or a probability of the sex of the pupa).

At block 760, the computing device 150 stores records for the sensed insect pupae. In one example, the computing device 150 may store aggregated information for a particular pupae population, such as population-level statistics for size, sex, abnormalities, etc. In some examples, the computing device 150 may store an individual record for each insect pupae, which may include an identification number (e.g., a population number in combination with a count number), an image of the pupa (if available), and one or more detected characteristics of the pupa, such as a size, sex, etc. Such information may enable individualized review of a particular population. For example, the records may be filtered to enable review of insect pupae having a below-normal size, one or more physical abnormalities, etc.

Figure 8:
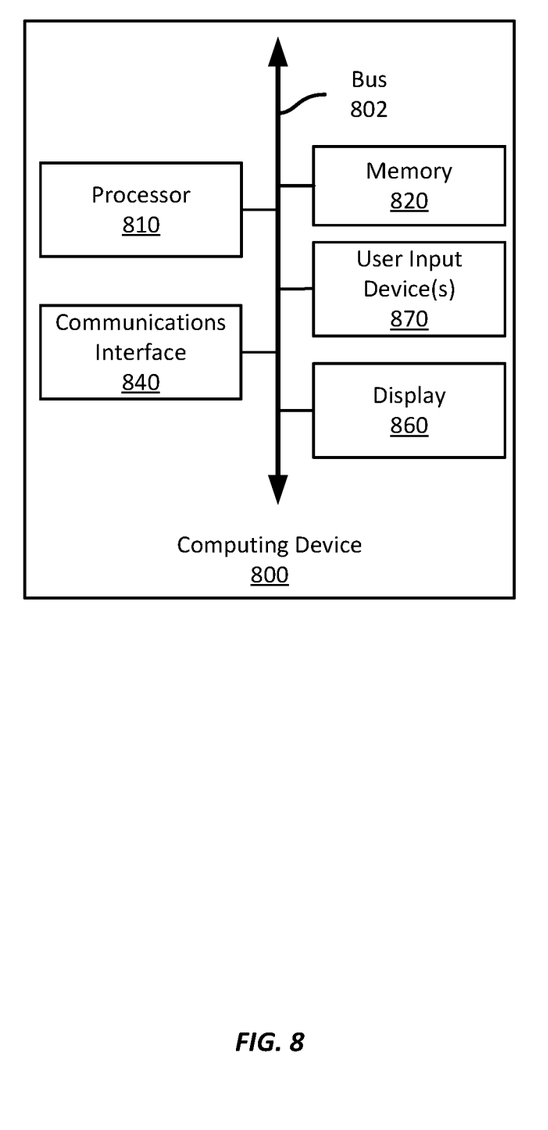
FIG. 8 shows an example computing device for continuous insect pupae sensing according to this disclosure.

Referring now to FIG. 8, FIG. 8 shows an example computing device 800 suitable for use in example systems or methods for continuous insect pupae sensing according to this disclosure. The example computing device 800 includes a processor 810 which is in communication with the memory 820 and other components of the computing device 800 using one or more communications buses 802. The processor 810 is configured to execute processor-executable instructions stored in the memory 820 to provide continuous insect pupae sensing, such as part or all of the example method 700 described above with respect to FIG. 7. The computing device 800, in this example, also includes one or more user input devices 870, such as a keyboard, mouse, touchscreen, microphone, etc., to accept user input. The computing device 800 also includes a 860 display to provide visual output to a user.

The computing device 800 also includes a communications interface 840. In some examples, the communications interface 840 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure.

The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   receiving a flow at a singulator, the flow comprising a liquid and a plurality of insects;
   singulating the insects into a single-file flow of insects;
   sensing, using a sensor, insects within the single-file flow of insects; and
   incrementing a counter based on each sensed insects in the single-file flow of insects.

2. The method of claim 1, wherein the flow comprises water and the plurality of insects.

3. The method of claim 1, wherein the flow is carried by a conveyor belt.

4. The method of claim 1, wherein the sensor comprises a camera.

5. The method of claim 4, further comprising capturing an image of an insect, and determining a characteristic of the insect based on the image.

6. The method of claim 5, wherein the characteristic comprises a sex, a size, or an anomaly.

7. The method of claim 6, further comprising capturing an image of each sensed insects, and determining one or more characteristics of each sensed insects.

8. The method of claim 5, further comprising creating and storing a record for the insect, the record comprising the characteristic and the image.

9. The method of claim 1, wherein the sensor comprises a photodetector.

10. The method of claim 1, wherein the sensor comprises two conductive plates and sensing the insects comprises determining a change in capacitance between the two conductive plates.

11. The method of claim 1, wherein the singulator comprises an hourglass shape having a neck portion, the neck portion sized to allow a single insects to pass at a time, and wherein singulating the insects comprises applying a substantially constant pressure to the flow of insects.

12. The method of claim 1, wherein the singulator comprises a first and second sheet of material, the first sheet of material positioned below the second sheet forming a wedge arrangement using the first and second sheets of material, and oriented such that a gap between the first and second sheets of material within the wedge arrangement narrows from one edge of the first sheet to the opposite end to a width of a single insects.

13. The method of claim 1, wherein the singulator comprises a channel and an air outlet, and wherein singulating the insects comprises flowing the flow of insects through the channel, and forming one or more bubbles in the flow of insects between insects by outputting puffs of air from the air outlet.

14. The method of claim 1, further comprising receiving the flow of insects at a plurality of singulators in parallel, and at each singulator:
   singulating the insects from the received flow of insects into a single-file flow of insects;
   sensing insects within the single-file flow of insects; and
   incrementing the counter associated based on a number of sensed insects in the respective single-file flow of insects.

15. A system comprising:
   a channel defining a flow path for a flow of insects, the flow comprising a liquid and a plurality of insects;
   a singulator positioned within the flow path and arranged to receive the flow of insects within the channel, the singulator configured to singulate the insects into a single-file flow of insects;
   a sensor positioned and arranged to sense insects in the single-file flow; and
   a processor in communication with the sensor and a non-transitory computer-readable medium, the processor configured to execute processor-executable instructions stored in the non-transitory computer-readable medium to:
      receive sensor signals from the sensor; and
      count a number of insects based on the received sensor signals.

16. The system of claim 15, wherein the flow of insects comprises water and one or more insects.

17. The system of claim 15, further comprising a conveyor belt defining the channel, wherein the conveyor belt is configured to convey the flow of insects.

18. The system of claim 15, wherein the sensor comprises a camera.

19. The system of claim 18, wherein the processor is configured to execute processor-executable instructions stored in the non-transitory computer-readable medium to:
   receive an image of an insect, and
   determine a characteristic of the insect based on the image.

20. The system of claim 19, wherein the characteristic comprises a sex, a size, or an anomaly.

21. The system of claim 20, wherein the processor is configured to execute processor-executable instructions stored in the non-transitory computer-readable medium to:
   receive images of each sensed insects, and
   determine one or more characteristics of each sensed insects.

22. The system of claim 19, wherein the processor is configured to execute processor-executable instructions stored in the non-transitory computer-readable medium to create and store a record for the insect, the record comprising the characteristic and the image.

23. The system of claim 15, wherein the sensor comprises a photodetector.

24. The system of claim 15, wherein the sensor comprises two conductive plates and the sensor signals comprises an indication of capacitance, and wherein the processor is configured to execute processor-executable instructions stored in the non-transitory computer-readable medium to:
   determine a change in capacitance between the two conductive plates based on the received sensor signals, and
   count the number of insects based on the change in capacitance.

25. The system of claim 15, wherein the singulator comprises an hourglass shape having a neck portion, the neck portion sized to allow a single insects to pass at a time, and wherein the system is configured to apply a substantially constant pressure to the flow of insects.

26. The system of claim 15, wherein the singulator comprises a first and second sheet of material, the first sheet of material positioned below the second sheet forming a wedge arrangement using the first and second sheets of material, and oriented such that a gap between the first and second sheets of material within the wedge arrangement narrows from one edge of the first sheet to the opposite end to a width of a single insects.

27. The system of claim 15, wherein the system comprises an air source and the singulator comprises an air outlet, and wherein the singulator is configured output puffs of air from the air outlet to form one or more bubbles in the flow of insects between insects.

28. The system of claim 15, further comprising a plurality of singulators arranged in parallel to each other, and a plurality of sensors, at least one sensor of the plurality of sensors positioned at each singulator of the plurality of singulators, and wherein the processor is configured to execute processor-executable instructions stored in the non-transitory computer-readable medium to:
receive sensor signals from each of the plurality of sensors, and
count the number of insects based on the received sensor signals from each of the plurality of sensors.

29. The system of claim 15, wherein the processor is a first processor and further comprising a second processor, the second processor configured to receive one or more sensor signals, determine a characteristic of an insect based on the one or more sensor signals, and provide the characteristic to the first processor.

* * * * *